(12) United States Patent
Nakayama et al.

(10) Patent No.: US 10,407,448 B2
(45) Date of Patent: Sep. 10, 2019

(54) N-N-BIS(2-DIALKYLPHOSPHINOETHYL) AMINE-BORANE COMPLEX AND PRODUCTION METHOD THEREFOR, AND METHOD FOR PRODUCING RUTHENIUM COMPLEX CONTAINING N,N-BIS(2-DIALKYLPHOSPHINOETHYL) AMINE AS LIGAND

(71) Applicant: Takasago International Corporation, Tokyo (JP)

(72) Inventors: Yuji Nakayama, Kanagawa (JP); Hikaru Nakajima, Kanagawa (JP)

(73) Assignee: Takasago International Corporation, Tokyo (JP)

(*) Notice: Subject to any disclaimer, the term of this patent is extended or adjusted under 35 U.S.C. 154(b) by 0 days.

(21) Appl. No.: 16/073,660

(22) PCT Filed: Jan. 30, 2017

(86) PCT No.: PCT/JP2017/003116
§ 371 (c)(1),
(2) Date: Jul. 27, 2018

(87) PCT Pub. No.: WO2017/131226
PCT Pub. Date: Aug. 3, 2017

(65) Prior Publication Data
US 2019/0040090 A1 Feb. 7, 2019

(30) Foreign Application Priority Data
Jan. 29, 2016 (JP) ................ 2016-016455

(51) Int. Cl.
*C07F 9/50* (2006.01)
*C07F 9/28* (2006.01)
(Continued)

(52) U.S. Cl.
CPC ............ *C07F 9/5077* (2013.01); *C07F 5/022* (2013.01); *C07F 9/28* (2013.01); *C07F 9/5027* (2013.01); *C07F 15/0046* (2013.01)

(58) Field of Classification Search
None
See application file for complete search history.

(56) References Cited

U.S. PATENT DOCUMENTS

| 2011/0237814 A1 | 9/2011 | Kuriyama et al. |
| 2013/0172619 A1 | 7/2013 | Ogata et al. |

(Continued)

FOREIGN PATENT DOCUMENTS

| JP | 2012-67021 A | 4/2012 |
| JP | 2014-114257 A | 6/2014 |

(Continued)

OTHER PUBLICATIONS

A.A. Danopoulos et al., "The Synthesis of Tridentate Dialkylamino Ligands Containing Tertiary Phosphorus or Arsenic Donors", Polyhedron, 9(19), pp. 2413-2418 (1990).

(Continued)

*Primary Examiner* — Amy C Bonaparte
(74) *Attorney, Agent, or Firm* — Mintz Levin Cohn Ferris Glovsky and Popeo, P.C.; Peter F. Corless (57) ABSTRACT

The purpose of the present invention is to provide an N,N-bis(2-dialkylphosphinoethyl)amine-borane complex which is a ruthenium complex that exhibits excellent catalytic activity in a hydrogenation reaction, etc., and a production method therefor, and a method for efficiently producing a ruthenium complex containing N,N-bis(2-dialkylphosphinoethyl)amine as a ligand. The present invention is capable of efficiently producing an amine-borane complex (3) by reacting an oxazolidinone compound

(Continued)

(1) with a dialkylphosphine-borane compound (2) in the presence of a base. The present invention is also capable of efficiently producing a ruthenium complex (5) by reacting the amine-borane complex (3) with a ruthenium compound (4) in the presence of an amine.

(In the formula, a solid line, a dashed line, B, C, H, $L^1$-$L^3$, LG, n, N, O, P, Ru, X, and $R^1$-$R^{10}$ are as defined in the description.)

11 Claims, 2 Drawing Sheets

(51) Int. Cl.
C07F 5/02 (2006.01)
C07F 15/00 (2006.01)

(56) References Cited

U.S. PATENT DOCUMENTS

2014/0163257 A1 6/2014 Hori et al.
2014/0303374 A1 10/2014 Touge et al.
2016/0009632 A1 1/2016 Ogata et al.
2016/0288111 A1 10/2016 Dumeignil et al.

FOREIGN PATENT DOCUMENTS

| JP | 2014-519472 A | 8/2014 |
| WO | 2008/141439 A1 | 11/2008 |
| WO | 2011/048727 A1 | 4/2011 |
| WO | 2012/144650 A1 | 10/2012 |
| WO | 2014/136374 A1 | 9/2014 |
| WO | 2015/067899 A1 | 5/2015 |

OTHER PUBLICATIONS

M. Nielsen et al., "Efficient Hydrogen Production from Alcohols under Mild Reaction Conditions", Angew. Chem. Int. Ed., vol. 50, pp. 9593-9597 (2011).
Z. Han et al., "Catalytic Hydrogenation of Cyclic Carbonates: A Practical Approach from CO2 and Epoxides to Methanol and Diols", Angew. Chem. Int. Ed., vol. 51, pp. 13041-13045 (2012).
L. Zhang et al., "Highly Efficient Ruthenium-Catalyzed N-Formylation of Amines with H2 and CO2", Angew. Chem. Int. Ed., vol. 54, pp. 6186-6189 (2015).
F. Schneck et al., "Selective Hydrogenation of Amides to Amines and Alcohols Catalyzed by Improved Iron Pincer Complexes", Organometallics, vol. 35, pp. 1931-1943 (2016).
International Preliminary Report on Patentability issued in corresponding International Application No. PCT/JP2017/003116, dated Jul. 31, 2018, 11 pages.

N-N-BIS(2-DIALKYLPHOSPHINOETHYL) AMINE-BORANE COMPLEX AND PRODUCTION METHOD THEREFOR, AND METHOD FOR PRODUCING RUTHENIUM COMPLEX CONTAINING N,N-BIS(2-DIALKYLPHOSPHINOETHYL)AMINE AS LIGAND

RELATED APPLICATIONS

This application is the U.S. national stage pursuant to 35 U.S.C. § 371, of Japanese international application Ser. No. PCT/JP2017/003116, filed Jan. 30, 2017 and published in Japanese on Aug. 3, 2017 as publication WO 2017/131226 A1, which claims the benefit of priority of Japanese Application No. 2016-016455, filed Jan. 29, 2016, which are hereby expressly incorporated by reference in their entirety.

TECHNICAL FIELD

The present invention relates to an N,N-bis(2-dialkylphosphinoethyl)amine-borane complex, and a production method therefor, and a method for producing a ruthenium complex containing N,N-bis(2-dialkylphosphinoethyl) amines as a ligand.

BACKGROUND ART

Various metal complexes comprising metal species and ligands are widely used as catalysts for organic synthesis reactions. Not only the metal species but also the ligand in the metal complex, which is an organic compound having a group (coordination group) having lone pair electrons capable of coordinating to the metal species plays an extremely important role, is known as a factor for the expression of the performance and activity of such a catalyst. Especially, metal complexes with tridentate ligand having an imino group as a coordination group in the molecule are known to exhibit high catalytic activities in, for example, hydrogenation reactions of carbonyl compounds, dehydrogenation reactions of alcohols, and the like, and also the hydrogen atom on the imino group is known to exert great influences on the expression of activities in these catalytic organic synthesis reactions. Known examples of such a tridentate ligand include N,N-bis(2-phosphinoethyl) amine, and it is reported that ruthenium complexes with the tridentate ligand function as excellent catalysts in hydrogenation reactions of esters (Patent Documents 1 to 4 and Non-Patent Documents 1 to 3). N,N-bis(2-diarylphosphinoethyl)amines used as a ligand can be synthesized easily by introducing phosphino groups as the coordination groups to N,N-bis(2-chloroethyl)amine as a substrate. On the other hand, in the case of synthesizing N,N-bis(2-dialkylphosphinoethyl)amine having an alkyl group substituted on phosphorus, since the yield is low in the foregoing method, there has been developed a method of protecting an imino group of N,N-bis(2-chloroethyl)amine with a trimethylsilyl group to provide N,N-bis(2-chloroethyl)trimethylsilylamine and introducing dialkylphosphino groups at an extremely low temperature (Non-Patent Document 4). However, this production method has problems such that purification is difficult because N,N-bis(2-chloroethyl)trimethylsilylamine of a substrate is decomposed during distillation, that an expensive silylating agent is necessary, that operation at a cryogenic temperature is necessary, and that troublesome operation such as degassing operation is necessary because N,N-bis(2-dialkylphosphinoethyl)amine obtained is unstable to air.

As a method for producing a ruthenium complex containing N,N-bis(2-dialkylphosphinoethyl)amine as a ligand, a production method using $RuHCl(CO)(PPh_3)_3$ as a precursor and the like are known; however, this method has disadvantageous problems for industrialization such that a troublesome operation is required because the ligand is unstable to air, and that reaction at high temperature for a long time is required.

Thus, there has been desired a method for producing N,N-bis(2-dialkylphosphinoethyl)amines and a ruthenium complex with the N,N-bis(2-dialkylphosphinoethyl)amine, which is suitable for industrialization and is practical, and does not have the problems as described above, that is, which allows short production process, mild reaction conditions, and easy production with high yield.

CITATION LIST

Patent Document

Patent Document 1: WO 2011/048727 A1
Patent Document 2: JP 2012-067021 A
Patent Document 3: JP 2014-519472 A
Patent Document 4: JP 2014-114257 A

Non-Patent Document

Non-Patent Document 1: Lei Zhang, Zhaobin Han, Xiaoyu Zhao, Zheng Wang, and Kuiling Ding, Angew. Chem. Int. Ed. Ingl., 2015, 54, 6186.
Non-Patent Document 2: Zhaobin Han, Liangce Rong, Jiang Wu, Lei Zhang, Zheng Wang, and Kuiling Ding, Angew. Chem. Int. Ed. Ingl. 2012, 51, 13041.
Non-Patent Document 3: Martin Nielsen, Anja Kammer, Daniela Cozzula, Henrik Junge, Serafino Gladiali, Matthias Beller, Angew. Chem. Int. Ed. Ingl., 2011, 50, 9593.
Non-Patent Document 4: A. A. Danopoulos, A. R. Wills, P. G. Edwards, Polyhedron, 1990, 9, 2413.

SUMMARY OF THE INVENTION

Problems to be Solved by the Invention

An object of the present invention is to provide a production method in which a ruthenium metal complex containing, as a ligand, N,N-bis(2-dialkylphosphinoethyl) amines having excellent performance such as catalytic activity in a hydrogenation reaction of a carbonyl compound, a dehydrogenation reaction of alcohols, etc. can be produced in a simple manner and high yield. Further, it is an object of the present invention to provide an N,N-bis(2-dialkylphosphinoethyl)amine-borane complex which is useful as a ligand raw material and a novel method for safely and practically producing the same.

Means for Solving the Problems

The present inventors have conducted intensive study to solve the above-described problems, and consequently have found that carbon dioxide is reacted with N,N-bis(2-chloroethyl)amine to be derived to 3-(2-chloroethyl)-2-oxazolidinone, and thus to react a dialkylphosphine-borane compound with the reaction product in the presence of bases, whereby a novel N,N-bis(2-dialkylphosphinoethyl)amine- borane complex can be synthesized with good yield by simple operation. It has been found that this novel compound is stable to air and can be easily purified by, for example, column chromatography or recrystallization, and by reacting this compound with a ruthenium precursor in the presence of amines, a ruthenium metal complex containing, as a ligand, N,N-bis(2-dialkylphosphinoethyl)amines having excellent performance such as catalytic activity in a hydrogenation reaction of a carbonyl compound, a dehydrogenation reaction of alcohols, etc. can be safely produced in high yield by a short process, and the present invention has been completed.

Namely, the present invention provides an N,N-bis(2-dialkylphosphinoethyl)amine-borane complex, and a production method therefor, and a method for producing a ruthenium complex containing N,N-bis(2-dialkylphosphinoethyl)amines as a ligand.

That is, the present invention includes the following [1] to [11].

[1] A method for producing a compound having the following formula (3):

[Chemical Formula 3]

wherein the solid line represents a single bond; B represents a boron atom, C represents a carbon atom, H represents a hydrogen atom, N represents a nitrogen atom, and P represents a phosphorus atom; $R^1$ and $R^2$ each independently represent an optionally substituted alkyl group or an optionally substituted cycloalkyl group; $R^1$ and $R^2$, which are adjacent to each other, may bind together to form an optionally substituted ring; $R^3$, $R^4$, $R^5$, $R^6$, $R^7$, $R^8$, $R^9$ and $R^{10}$ each independently represent a hydrogen atom or a group selected from the group consisting of an optionally substituted alkyl group, an optionally substituted cycloalkyl group, an optionally substituted alkenyl group, an optionally substituted aryl group, and an optionally substituted aralkyl group; $R^3$ to $R^{10}$ may bind together to form an optionally substituted ring; n=2 to 3, and $BH_3$ is coordinated to a nitrogen atom or phosphorus atom, the method comprising: reacting a compound having the following formula (1):

[Chemical Formula 1]

wherein the solid line represents a single bond, and the double line represents a double bond; C represents a carbon atom, N represents a nitrogen atom, and O represents an oxygen atom; LG represents a leaving group; $R^3$, $R^4$, $R^5$, $R^6$, $R^7$, $R^8$, $R^9$ and $R^{10}$ each independently represent a hydrogen atom or a group selected from the group consisting of, an optionally substituted alkyl group, an optionally substituted cycloalkyl group, an optionally substituted alkenyl group, an optionally substituted aryl group, and an optionally substituted aralkyl group; and $R^3$ to $R^{10}$ may bind together to form an optionally substituted ring, with a phosphorus compound having the following formula (2):

[Chemical Formula 2]

wherein the solid line represents a single bond, and the dashed line represents a coordination bond; B represents a boron atom, H represents a hydrogen atom, and P represents a phosphorus atom; $R^1$ and $R^2$ each independently represent an optionally substituted alkyl group or an optionally substituted cycloalkyl group; and $R^1$ and $R^2$, which are adjacent to each other, may bind together to form an optionally substituted ring, in the presence of bases.

[2] The method according to [1], wherein $R^3$, $R^4$, $R^5$, $R^6$, $R^7$, $R^8$, $R^9$ and $R^{10}$ are hydrogen atoms.

[3] The method according to [1] or [2], wherein $R^1$ and $R^2$ are compounds each independently selected from the group consisting of an isopropyl group, a cyclohexyl group, and a tert-butyl group.

[4] The method according to any one of [1] to [3], wherein LG is a halogen atom or a group selected from the group consisting of a methanesulfonyloxy group (OMs), a p-toluenesulfonyloxy group (OTs), a benzenesulfonyloxy group ($OSO_2C_6H_5$), and a trifluoromethanesulfonyloxy group (OTf).

[5] The method according to any one of [1] to [4], wherein the base is alkyllithium.

[6] A method for producing a ruthenium complex having the following formula (5):

[Chemical Formula 6]

wherein the solid line represents a single bond, the triple line represents a triple bond, and the dashed line represents a coordination bond; C represents a carbon atom, H represents a hydrogen atom, N represents a nitrogen atom, O represents an oxygen atom, P represents a phosphorus atom, and Ru represents a ruthenium atom; X represents an anionic group; $R^1$ and $R^2$ each independently represent an optionally substituted alkyl group or an optionally substituted cycloalkyl group; $R^1$ and $R^2$, which are adjacent to each other, may bind together to form an optionally substituted ring; $R^3$, $R^4$, $R^5$, $R^6$, $R^7$, $R^8$, $R^9$ and $R^{10}$ each independently represent a hydrogen atom or a group selected from the group consisting of an optionally substituted alkyl group, an optionally substituted cycloalkyl group, an optionally substituted alkenyl group, an optionally substituted aryl group, and an optionally substituted aralkyl group; and $R^3$ to $R^{10}$ may bind together to form an optionally substituted ring, the method comprising: reacting a compound having the following formula (3):

[Chemical Formula 4]

(3)

wherein the solid line represents a single bond; B represents a boron atom, C represents a carbon atom, H represents a hydrogen atom, N represents a nitrogen atom, and P represents a phosphorus atom; $R^1$ and $R^2$ each independently represent an optionally substituted alkyl group or an optionally substituted cycloalkyl group; $R^1$ and $R^2$, which are adjacent to each other, may bind together to form an optionally substituted ring; $R^3$, $R^4$, $R^5$, $R^6$, $R^7$, $R^8$, $R^9$ and $R^{10}$ each independently represent a hydrogen atom or a group selected from the group consisting of an optionally substituted alkyl group, an optionally substituted cycloalkyl group, an optionally substituted alkenyl group, an optionally substituted aryl group, and an optionally substituted aralkyl group; $R^3$ to $R^{10}$ may bind together to form an optionally substituted ring; n=2 to 3, and $BH_3$ is coordinated to a nitrogen atom or phosphorus atom, with a ruthenium compound having the following formula (4):

[Chemical Formula 5]

(4)

wherein the solid line represents a single bond, the triple line represents a triple bond, and the dashed line represents a coordination bond; C represents a carbon atom, H represents a hydrogen atom, O represents an oxygen atom, and Ru represents a ruthenium atom; X represents an anionic group; and $L^1$, $L^2$, and $L^3$ each independently represent a monodentate ligand, in the presence of amines.

[7] The method according to [6], wherein $R^3$, $R^4$, $R^5$, $R^6$, $R^7$, $R^8$, $R^9$ and $R^{10}$ are hydrogen atoms.

[8] The method according to [6] or [7], wherein $R^1$ and $R^2$ are compounds each independently selected from the group consisting of an isopropyl group, a cyclohexyl group, and a tert-butyl group.

[9] The method according to any one of [6] to [8], wherein $L^1$, $L^2$, and $L^3$ are tertiary phosphines.

[10] The method according to any one of [6] to [9], wherein X is a halogen atom.

[11] A compound having the following formula (3):

[Chemical Formula 7]

(3)

wherein the solid line represents a single bond; B represents a boron atom, C represents a carbon atom, H represents a hydrogen atom, N represents a nitrogen atom, and P represents a phosphorus atom; $R^1$ and $R^2$ each independently represent an optionally substituted alkyl group or an optionally substituted cycloalkyl group; $R^1$ and $R^2$, which are adjacent to each other, may bind together to form an optionally substituted ring; $R^3$, $R^4$, $R^5$, $R^6$, $R^7$, $R^8$, $R^9$ and $R^{10}$ each independently represent a hydrogen atom or a group selected from the group consisting of an optionally substituted alkyl group, an optionally substituted cycloalkyl group, an optionally substituted alkenyl group, an optionally substituted aryl group, and an optionally substituted aralkyl group; $R^3$ to $R^{10}$ may bind together to form an optionally substituted ring; n=2 to 3, and $BH_3$ is coordinated to a nitrogen atom or phosphorus atom.

Effects of the Invention

The present invention provides a method for simply and practically producing a novel N,N-bis(2-dialkylphosphinoethyl)amine-borane complex. The N,N-bis(2-dialkylphosphinoethyl)amine-borane complex according to the present invention is stable to air and can be easily purified by, for example, column chromatography or recrystallization, and by reacting this complex with a ruthenium precursor in the presence of amines, a ruthenium metal complex containing, as a ligand, N,N-bis(2-dialkylphosphinoethyl)amines having excellent performance such as catalytic activity in a hydrogenation reaction of a carbonyl compound, a dehydrogenation reaction of alcohols, etc. can be safely produced in high yield by a short process.

DESCRIPTION OF EMBODIMENTS

Hereinafter, the present invention will be described in detail.

A method for producing an N,N-bis(2-dialkylphosphinoethyl)amine-borane complex having the formula (3) according to the present invention can be expressed by the following reaction formula (6).

[Chemical Formula 8]

In the oxazolidinone having the above formula (1), the leaving group represented by LG may be any group that enables a nucleophilic substitution reaction, specific examples thereof include halogen atoms such as a fluorine atom, a chlorine atom, a bromine atom, and an iodine atom, a methanesulfonyloxy group (OMs), a p-toluenesulfonyloxy group (OTs), a benzenesulfonyloxy group ($OSO_2C_6H_5$), and a trifluoromethanesulfonyloxy group (OTf), of which a halogen atom is preferable and a chlorine atom is more preferable.

$R^3$, $R^4$, $R^5$, $R^6$, $R^7$, $R^8$, $R^9$ and $R^{10}$ each independently represent a hydrogen atom or a group selected from the group consisting of an alkyl group optionally having substituent(s), a cycloalkyl group optionally having substituent(s), an alkenyl group optionally having substituent(s), an aryl group optionally having substituent(s), and an aralkyl group optionally having substituent(s), and preferably each represent a hydrogen atom.

The alkyl group in $R^3$ to $R^{10}$ may be linear or branched, examples thereof include an alkyl group having 1 to 30 carbon atoms, preferably 1 to 20 carbon atoms, and more preferably 1 to 10 carbon atoms, and specific examples thereof include a methyl group, an ethyl group, an n-propyl group, an isopropyl group, an n-butyl group, a 2-butyl group, an isobutyl group, a tert-butyl group, a cyclobutyl group, an n-pentyl group, a 2-pentyl group, a 3-pentyl group, a tert-pentyl group, a 2-methylbutyl group, a 3-methylbutyl group, a 2-methylbutan-3-yl group, a 2,2-dimethylpropyl group, an n-hexyl group, a 2-hexyl group, a 3-hexyl group, a tert-hexyl group, a 2-methylpentyl group, a 3-methylpentyl group, a 4-methylpentyl group, a 2-methylpentane-3-yl group, a 2-methylpentan-4-yl group, a 3-methylpentan-2-yl group, a 3-methylpentan-3-yl group, a 2,2-dimethylbutyl group, a 3,3-dimethylbutyl group, a 2,2-dimethylbutan-3-yl group, an n-heptyl group, an n-octyl group, an n-nonyl group, an n-decyl group, an n-dodecyl group, and an n-hexadecyl group, of which a methyl group, an ethyl group, an isopropyl group, and a tert-butyl group are preferable.

Examples of the cycloalkyl group include a saturated or unsaturated monocyclic or polycyclic cycloalkyl group having 3 to 8 carbon atoms, preferably 5 to 7 carbon atoms. Examples of such a cycloalkyl group include a cyclopropyl group, a cyclopentyl group, a cyclohexyl group, a 1-adamantyl group, and a 2-adamantyl group, of which a cyclopentyl group and a cyclohexyl group are preferable.

Examples of the alkenyl group include an alkenyl group having 2 to 20 carbon atoms, which may be linear, branched or cyclic, of which an alkenyl group having 2 to 14 carbon atoms is preferable and an alkenyl group having 2 to 8 carbon atoms is more preferable. Specific examples thereof include a vinyl group, a 1-propenyl group, a 2-propenyl group, an allyl group, a 1-cyclohexenyl group, a 1-styryl group, and a 2-styryl group.

Examples of the aryl group include an aryl group having 6 to 18 carbon atoms, of which an aryl group having 6 to 14 carbon atoms is preferable and an aryl group having 6 to 10 carbon atoms is more preferable. Specific examples thereof include a phenyl group, a 1-naphthyl group, and a 2-naphthyl group, and preferred specific examples thereof include a phenyl group.

Examples of the aralkyl group include an aralkyl group having the above-described alkyl group in which at least one hydrogen atom of the alkyl group is substituted with the above-described aryl group and a polycyclic aralkyl group formed by condensing the above-described cyclic alkyl group with the above-described aryl group, and specific examples thereof include a benzyl group, a 1-phenylethyl group, a 2-phenylethyl group, a 1-phenylpropyl group, a 2-phenylpropyl group, a 3-phenylpropyl group, a 1-phenyl-2-propyl group, a 2-phenyl-2-propyl group, a 1-indanyl group, a 2-indanyl group, and a 9-fluorenyl group.

Substituents which may be present on the alkyl groups, the cycloalkyl groups, the alkenyl groups, the aryl groups, and the aralkyl group serving as $R^3$ to $R^{10}$, the ring formed when two of the $R^3$ to $R^6$ are bonded to each other, the ring formed when two of the $R^7$ to $R^{10}$ are bonded to each other, and the ring formed when two of the $R^3$ to $R^{10}$ are bonded to each other include alkyl groups, halogen atoms, alkenyl groups, aryl groups, heteroaryl groups, aralkyl groups, halogenoalkyl groups, and alkoxy groups, and the alkyl groups, the halogen atoms, the alkenyl groups, the aryl groups, the aralkyl groups, and substituent groups thereon are the same as those described in detail above.

The heteroaryl groups include heteroaryl groups derived from 5- or 6-membered aromatic heterocycles containing 1 to 4 heteroatoms selected from the group consisting of a nitrogen atom, an oxygen atom, and a sulfur atom, and heteroaryl groups derived from polycyclic aromatic heterocycles which are formed by condensing the above-described aromatic heterocycles with the above-described aryl groups. Specific examples thereof include a 2-furyl group, a 3-furyl group, a 2-thienyl group, a 3-thienyl group, a 2-benzofuryl group, a 3-benzofuryl group, a 2-benzothienyl group, and a 3-benzothienyl group.

Examples of the alkoxy groups include alkoxy groups having 1 to 10 carbon atoms, of which alkoxy groups having 1 to 4 carbon atoms are preferable. Specific examples thereof include a methoxy group, an ethoxy group, a 1-propoxy group, a 2-propoxy group, a 1-butoxy group, a 2-butoxy group, and a tert-butoxy group.

Examples of the halogenoalkyl groups include groups which are the same as the above-described alkyl groups, except that at least one hydrogen atom is replaced with a halogen atom, and specific examples thereof include a trifluoromethyl group, and an n-nonafluorobutyl group.

In the phosphine-borane complex having the above formula (2), $R^1$ and $R^2$ each independently represent an alkyl group optionally having substituent(s) or a cycloalkyl group optionally having substituent(s).

The alkyl group in $R^1$ and $R^2$ may be linear or branched, examples thereof include an alkyl group having 1 to 30 carbon atoms, preferably 1 to 20 carbon atoms, and more preferably 1 to 10 carbon atoms, and specific examples thereof include a methyl group, an ethyl group, an n-propyl group, an isopropyl group, an n-butyl group, a 2-butyl group, an isobutyl group, a tert-butyl group, a cyclobutyl group, an n-pentyl group, a 2-pentyl group, a 3-pentyl group, a tert-pentyl group, a 2-methylbutyl group, a 3-methylbutyl group, a 2-methylbutan-3-yl group, a 2,2-dimethylpropyl group, an n-hexyl group, a 2-hexyl group, a 3-hexyl group, a tert-hexyl group, a 2-methylpentyl group, a 3-methylpentyl group, a 4-methylpentyl group, a 2-methylpentane-3-yl group, a 2-methylpentan-4-yl group, a 3-methylpentan-2-yl group, a 3-methylpentan-3-yl group, a 2,2-dimethylbutyl group, a 3,3-dimethylbutyl group, a 2,2-dimethylbutan-3-yl group, an n-heptyl group, an n-octyl group, an n-nonyl group, an n-decyl group, an n-dodecyl group, and an n-hexadecyl group, of which a methyl group, an ethyl group, an isopropyl group, and a tert-butyl group are preferable.

Examples of the cycloalkyl group in $R^1$ and $R^2$ include a saturated or unsaturated monocyclic or polycyclic cycloalkyl group having 3 to 8 carbon atoms, preferably 5 to 7 carbon atoms. Examples of such a cycloalkyl group include a cyclopropyl group, a cyclopentyl group, a cyclohexyl group, a 1-adamantyl group, and a 2-adamantyl group, of which a cyclopentyl group and a cyclohexyl group are preferable.

$R^1$ and $R^2$ may be bonded to each other to form an optionally substituted ring. Specific examples of such a ring include a phosphetane ring and a phospholane ring.

Substituents which may be present on the alkyl groups and the cycloalkyl groups serving as $R^1$ and $R^2$ and the ring formed when $R^1$ and $R^2$ are bonded to each other include alkyl groups, halogen atoms, alkenyl groups, aryl groups, heteroaryl groups, aralkyl groups, halogenoalkyl groups, and alkoxy groups, and the alkyl groups, the halogen atoms, the alkenyl groups, the aryl groups, the aralkyl groups, and these substituents are the same as those described in detail in the above formula (1).

In the N,N-bis(2-dialkylphosphinoethyl)amine-borane complex having the above formula (3), examples of an optionally substituted alkyl group represented by $R^1$ or $R^2$, an optionally substituted cycloalkyl group represented by $R^1$ or $R^2$, and an optionally substituted ring formed by bonding adjacent $R^1$ and $R^2$ to each other include the same groups as in the formula (2).

In the N,N-bis(2-dialkylphosphinoethyl)amine-borane complex having the above formula (3), $R^3$, $R^4$, $R^5$, $R^6$, $R^7$, $R^8$, $R^9$ and $R^{10}$ each independently represent a hydrogen atom or a group selected from the group consisting of an alkyl group optionally having substituent(s), a cycloalkyl group optionally having substituent(s), an alkenyl group optionally having substituent(s), an aryl group optionally having substituent(s), and an aralkyl group optionally having substituent(s), and preferably each represent a hydrogen atom. Examples of the alkyl group, the optionally substituted alkenyl group, the optionally substituted aryl group, and the optionally substituted aralkyl group in $R^3$ to $R^{10}$ include the same groups as in the above formula (1).

In the present invention, borane represents boron trihydride expressed by $BH_3$. In the formula (3), borane is coordinated to a nitrogen atom or phosphorus atom, and n is 2 or 3, or a mixture of 2 and 3. In the present specification, n=2 to 3 means that n=2, n=3 or a mixture thereof.

A method for producing the N,N-bis(2-dialkylphosphinoethyl)amine-borane complex having the above formula (3) will be described in detail.

The oxazolidinone having the formula (1) can be synthesized by a method similar to the known method in, for example, JP 2003-292798 A. For example, as shown in the reaction formula (7), 3-(2-chloroethyl)-2-oxazolidinone can be synthesized by reacting carbon dioxide with N,N-bis(2-chloroethyl)amine hydrochloride.

[Chemical Formula 9]

(7)

The phosphine-borane complex having the formula (2) can be synthesized by a method similar to the known method in, for example, Lydia McKinstry, Tom, Livinghouse, Tetrahedron, 1995, 51, 7655. As one example thereof, this complex can be produced by reacting secondary phosphines with a borane-dimethyl sulfide complex ($BH_3$—$SMe_2$), a borane-tetrahydrofuran complex ($BH_3$-THF), or the like.

The reaction of the oxazolidinone having the formula (1) and the phosphine-borane complex having the formula (2) produced as described above is carried out in the presence of bases, whereby the N,N-bis(2-dialkylphosphinoethyl)amine-borane complex having the formula (3) can be produced. The amount of the phosphine-borane complex having the formula (2) which is used is not particularly limited, and is selected, as appropriate, from the range of generally 0.6 to 20 equivalents, preferably 1 to 10 equivalents, and more preferably 2 to 5 equivalents to the oxazolidinone having the formula (1). The phosphine-borane complex having the formula (2) may be used after purification by, for example, column chromatography or recrystallization in the production process, and after extraction with a solvent, the solution washed with water may be used.

Specific examples of bases include alkali metal hydroxides such as lithium hydroxide, sodium hydroxide, and potassium hydroxide, alkaline earth metal hydroxides such as calcium hydroxide, strontium hydroxide, and barium hydroxide, metal hydrides such as lithium hydride, sodium hydride, potassium hydride, calcium hydride, sodium borohydride, and lithium aluminum hydride, alkali metal alkoxides such as lithium methoxide, sodium methoxide, potassium methoxide, sodium ethoxide, potassium ethoxide, sodium tert-butoxide, and potassium tert-butoxide, organolithium compounds such as methyllithium, n-butyllithium, sec-butyllithium, tert-butyllithium, and phenyllithium, alkali metal amides such as lithiumamide, sodium amide, lithium diisopropyl amide, and lithium hexamethyldisilazide, and Grignard reagents such as methylmagnesium chloride, tert-butylmagnesium chloride, phenylmagnesium chloride, phenylmagnesium bromide, and methylmagnesium iodide, of which alkyllithium is preferable. Particularly preferred specific examples thereof include n-butyllithium. Each of the bases may be used alone, or two or more of these bases may be used in combination, as appropriate.

The amount of the base used is not particularly limited, and is selected, as appropriate, from the range of generally 0.3 to 10 equivalents, preferably 0.5 to 5 equivalents, and more preferably 0.8 to 3 equivalents to the compound having the formula (2). In this reaction, a method for adding the base is not particularly limited, and each of the compound having the formula (2) and the base may be added separately. Alternatively, a mixture of the compound having the formula (2) and the base (and a solvent) may be added, or the phosphide-borane complex obtainable by reacting the compound having the formula (2) with the base (in a solvent) may be added.

This reaction is preferably carried out in the presence of solvent(s). Specific examples of the solvent include an aliphatic hydrocarbon such as n-pentane, n-hexane, n-heptane, n-octane, n-decane, cyclohexane, or decalin, an aromatic hydrocarbon such as benzene, toluene, xylene, mesitylene, p-cymene, or 1,4-diisopropylbenzene, a monoalcohol such as methanol, ethanol, 2-propanol, n-butanol, tert-butanol, 2-methyl-2-butanol, or 2-ethoxyethanol, a polyol such as ethylene glycol, propylene glycol, 1,2-propanediol, or glycerin, an ether such as diethyl ether, diisopropyl ether, tert-butyl methyl ether, cyclopentyl methyl ether, dimethoxyethane, ethylene glycol diethyl ether, tetrahydrofuran, or 1,4-dioxane, an amine such as triethylamine, aniline, or 2-phenethylamine. Preferred specific examples thereof include n-hexane and tetrahydrofuran. Each of the solvents may be used alone, or two or more of these solvents may be used in combination, as appropriate.

The amount of the solvent used is not particularly limited, and is selected, as appropriate, from the range of generally 1 to 200 volumes, preferably 2 to 100 volumes, and more preferably 5 to 50 volumes to 1 volume of the compound having the formula (1).

This reaction is preferably carried out in an inert gas atmosphere. Specific examples of the inert gas include argon gas and nitrogen gas. The reaction temperature is selected, as appropriate, from the range of generally −78 to 150° C., preferably −40 to 100° C., and more preferably −20 to 80° C. The reaction time naturally varies depending on the base, the solvent, the reaction temperature, and other conditions, and is selected, as appropriate, from the range of generally 1 minute to 48 hours, preferably 5 minutes to 24 hours, and more preferably 10 minutes to 15 hours.

If necessary, the thus obtained N,N-bis(2-dialkylphosphinoethyl)amine-borane complex having the formula (3) may be subjected to post treatments, isolation, and purification. Examples of methods for the post treatments include concentration, solvent exchange, washing, extraction, back-extraction, filtration, and crystallization by adding a poor solvent. These methods can be performed alone or in combination. Examples of methods for the isolation or purification include decolorization with an adsorbent, column chromatography, distillation, recrystallization, and crystallization of a salt obtained by washing of crystals with a poor solvent. These methods can be performed alone or in combination.

Next, a method for producing the ruthenium complex having the formula (5) can be expressed by the reaction formula (8). That is, the ruthenium complex can be produced by stirring the ruthenium carbonyl complex having the formula (4) and the N,N-bis(2-dialkylphosphinoethyl)amine-borane complex having the above formula (3) in the presence of amines, in a solvent as appropriate. The amount of the N,N-bis(2-dialkylphosphinoethyl)amine-borane complex having the formula (3) which is used is not particularly limited, and is selected, as appropriate, from the range of generally 0.5 to 20 equivalents, preferably 0.7 to 10 equivalents, and more preferably 0.8 to 3 equivalents to the ruthenium carbonyl complex having the formula (4).

[Chemical Formula 10]

In the formula (4), examples of the anionic group represented by X include a hydride ion (H$^-$); a halogen ion such as a chlorine ion (Cl$^-$), a bromine ion (Br$^-$), or an iodine ion (I$^-$); as well as complex anions such as BH$_4$, BF$_4$, BPh$_4$, PF$_6$, an acetoxy group, and a trifluoromethanesulfonyloxy group. A halogen ion is preferable, and a chlorine ion (Cl$^-$) is more preferable.

Examples of neutral monodentate ligands represented by L1, L2, and L3 include alcohols, ethers, sulfides, sulfoxides, amines, amides, nitriles, isonitriles, heteroarenes, secondary phosphines, secondary phosphine oxides, tertiary phosphines, phosphites, phosphoramidites, tertiary arsines, carbenes, hydrogen molecule, and carbon monoxide, of which tertiary phosphines, phosphites, carbon monoxide, and the like are more preferable. Tertiary phosphines and the like are still more preferable.

The tertiary phosphines are compounds having the following formula (9):

[Chemical Formula 11]

(9)

wherein P represents a phosphorus atom; $R^{11}$, $R^{12}$, and $R^{13}$ each independently represent a group selected from the group consisting of an alkyl group, an alkenyl group optionally having substituent(s), an aryl group optionally having substituent(s), a heteroaryl group optionally having substituent(s), and an aralkyl group optionally having substituent(s); and any two of $R^{11}$ to $R^{13}$ may be bonded to each other to form a ring optionally having substituent(s).

In the formula (9), P represents a phosphorus atom. $R^{11}$, $R^{12}$, and $R^{13}$ each independently represent a group selected from the group consisting of an optionally substituted alkyl group, an optionally substituted cycloalkyl group, an optionally substituted alkenyl group, an optionally substituted aryl group, an optionally substituted heteroaryl group, and an optionally substituted aralkyl group, and preferably represent a group selected from the group consisting of an alkyl group, an optionally substituted aryl group, and an optionally substituted heteroaryl group.

The alkyl groups may be linear or branched, and examples thereof include alkyl groups having 1 to 30 carbon atoms, of which alkyl groups having 1 to 20 carbon atoms are preferable and alkyl groups having 1 to 10 carbon atoms are more preferable. Specific examples thereof include a methyl group, an ethyl group, an n-propyl group, an isopropyl group, an n-butyl group, a 2-butyl group, an isobutyl group, a tert-butyl group, an n-pentyl group, a 2-pentyl group, a 3-pentyl group, a tert-pentyl group, a 2-methylbutyl group, a 3-methylbutyl group, a 2-methylbutan-3-yl group, a 2,2-dimethylpropyl group, an n-hexyl group, a 2-hexyl group, a 3-hexyl group, a tert-hexyl group, a 2-methylpentyl group, a 3-methylpentyl group, a 4-methylpentyl group, a 2-methylpentan-3-yl group, a 2-methylpentan-4-yl group, a 3-methylpentan-2-yl group, a 3-methylpentan-3-yl group, a 2,2-dimethylbutyl group, a 3,3-dimethylbutyl group, a 2,2-dimethylbutan-3-yl group, a cyclohexyl group, an n-heptyl group, an n-octyl group, an n-nonyl group, and an n-decyl group, and preferred specific examples thereof include a methyl group and an ethyl group.

Examples of the cycloalkyl group include a saturated or unsaturated monocyclic or polycyclic cycloalkyl group having 3 to 8 carbon atoms, preferably 5 to 7 carbon atoms. Examples of such a cycloalkyl group include a cyclopropyl group, a cyclobutyl group, a cyclopentyl group, a cyclohexyl group, a 1-adamantyl group, and a 2-adamantyl group, of which a cyclopentyl group and a cyclohexyl group are preferable.

Examples of the alkenyl group include an alkenyl group having 2 to 20 carbon atoms, which may be linear, branched or cyclic, of which an alkenyl group having 2 to 14 carbon atoms is preferable and an alkenyl group having 2 to 8 carbon atoms is more preferable. Specific examples thereof include a vinyl group, a 1-propenyl group, a 2-propenyl group, an allyl group, a 1-cyclohexenyl group, a 1-styryl group, and a 2-styryl group.

Examples of the aryl group include an aryl group having 6 to 18 carbon atoms, of which an aryl group having 6 to 14 carbon atoms is preferable and an aryl group having 6 to 10 carbon atoms is more preferable. Specific examples thereof include a phenyl group, a 1-naphthyl group, and a 2-naphthyl group, and preferred specific examples thereof include a phenyl group.

The heteroaryl groups include heteroaryl groups derived from 5- or 6-membered aromatic heterocycles containing 1 to 4 heteroatoms selected from the group consisting of a nitrogen atom, an oxygen atom, and a sulfur atom, and heteroaryl groups derived from polycyclic aromatic heterocycles which are formed by condensing the above-described aromatic heterocycles with the above-described aryl groups. Specific examples thereof include a 2-furyl group, a 3-furyl group, a 2-thienyl group, a 3-thienyl group, a 2-benzofuryl group, a 3-benzofuryl group, a 2-benzothienyl group, and a 3-benzothienyl group, and preferred specific examples thereof include a 2-furyl group.

Examples of the aralkyl group include an aralkyl group having the above-described alkyl group in which at least one hydrogen atom of the alkyl group is substituted with the above-described aryl group and a polycyclic aralkyl group formed by condensing the above-described cyclic alkyl group with the above-described aryl group, and specific examples thereof include a benzyl group, a 1-phenylethyl group, a 2-phenylethyl group, a 1-phenylpropyl group, a 2-phenylpropyl group, a 3-phenylpropyl group, a 1-phenyl-2-propyl group, a 2-phenyl-2-propyl group, a 1-indanyl group, a 2-indanyl group, and a 9-fluorenyl group.

Any two of $R^{11}$ to $R^{13}$ may be bonded to each other to form a ring optionally having substituent(s). Specific examples of the ring include a phospholane ring, a phosphole ring, a phosphinane ring, and a phosphinine ring.

Examples of substituents which may be present on the alkenyl groups, the aryl groups, the heteroaryl groups, and the aralkyl groups serving as $R^{11}$ to $R^{13}$ and on the ring formed when any two of $R^{11}$ to $R^{13}$ are bonded to each other include alkyl groups, halogenoalkyl groups, alkenyl groups, aryl groups, heteroaryl groups, aralkyl groups, hydroxy groups, alkoxy groups, alkoxycarbonyl groups, carboxyl groups, amino groups, sulfo groups, and halogeno groups. Of these substituents, the alkyl groups, alkenyl groups, aryl groups, heteroaryl groups, and aralkyl groups are the same as the groups in the detailed description of $R^{11}$ to $R^{13}$.

Examples of the halogenoalkyl groups include groups which are the same as the above-described alkyl groups, except that at least one hydrogen atom is replaced with a halogen atom. Specific examples thereof include a trifluoromethyl group and an n-nonafluorobutyl group, and preferred specific examples thereof include a trifluoromethyl group.

Examples of the alkoxy groups include alkoxy groups having 1 to 10 carbon atoms, of which alkoxy groups having 1 to 4 carbon atoms is preferable. Specific examples thereof include a methoxy group, an ethoxy group, a 1-propoxy group, a 2-propoxy group, a 1-butoxy group, a 2-butoxy group, and a tert-butoxy group, and preferred specific examples thereof include a methoxy group.

Specific examples of the alkoxycarbonyl groups include a methoxycarbonyl group.

Specific examples of the amino groups include a dimethylamino group and a 4-morpholinyl group.

Specific examples of the halogeno groups include a fluoro group, a chloro group, a bromo group, and an iodo group, of which a fluoro group and a chloro group are preferable.

Preferred specific examples of the tertiary phosphines having the formula (9) include trimethylphosphine, triethylphosphine, tricyclohexylphosphine, triphenylphosphine, tris(4-trifluoromethylphenyl)phosphine, tris(4-methoxyphenyl)phosphine, and tris(2-furyl)phosphine. Triphenylphosphine is more preferable.

Meanings of the each symbol of the substituent group included in the formula (5) are the same as those described above.

When used in the production of the ruthenium complex having the formula (5), borane of the N,N-bis(2-dialkylphosphinoethyl)amine-borane complex having the formula (3) is required to be dissociated. In the production of the ruthenium complex having the formula (5), borane may be used for complexation reaction while being dissociated in the reaction system. Preferably, the complexation reaction is carried out while dissociating borane in the reaction system. For the dissociation of borane, it is preferable to use a dissociation agent in combination, and as the dissociation agent for borane, any dissociation agent which is generally used may be used so long as it does not affect the complexation; however, amines are preferable.

Specific examples of the amines include diethylamine, triethylamine, tri-n-butylamine, diisopropylethylamine, N,N-dimethylaniline, 4-dimethylaminopyridine, pyrrolidine, piperidine, N-methylmorpholine, 1,5-diazabicyclo[4.3.0]non-5-ene (DBN), and 1,8-diazabicyclo[5.4.0]undec-7-ene (DBU), N,N,N',N'-tetramethylethylenediamine (TMEDA), and 1,4-diazabicyclo[2.2.2]octane (DABCO), of which diethylamine, N,N,N',N'-tetramethylethylenediamine (TMEDA), and 1,4-diazabicyclo[2.2.2]octane (DABCO) are preferable and 1,4-diazabicyclo[2.2.2]octane (DABCO) is more preferable.

The amount of the amines used is not particularly limited, and is selected, as appropriate, from the range of generally 0.5 to 30 equivalents, preferably 0.7 to 20 equivalents, and more preferably 0.8 to 10 equivalents to the compound having the formula (4). In this reaction, a method for adding the amines is not particularly limited, and each of the compound having the formula (3) and the base may be added separately, or a mixture of the compound having the formula (3) and the base (and a solvent) may be added.

This reaction is preferably carried out in the presence of solvent(s). Specific examples of the solvent include an aliphatic hydrocarbon such as n-pentane, n-hexane, n-heptane, n-octane, n-decane, cyclohexane, or decalin, an aromatic hydrocarbon such as benzene, toluene, xylene, mesitylene, p-cymene, or 1,4-diisopropylbenzene, a halogenated aromatic hydrocarbon such as chlorobenzene or o-dichlorobenzene, an alcohol such as methanol, ethanol, 2 propanol, n-butanol, tert-butanol, 2-methyl-2-butanol, or 2-ethoxyethanol, a polyol such as ethylene glycol, propylene glycol, 1,2-propanediol, or glycerin, an ether such as diethyl ether, diisopropyl ether, tert-butyl methyl ether, cyclopentyl methyl ether, dimethoxyethane, ethylene glycol diethyl ether, tetrahydrofuran, or 1,4-dioxane, an ester such as methyl acetate, ethyl acetate, n-butyl acetate, or methyl propionate, a ketone such as acetone, methyl ethyl ketone, methyl isobutyl ketone, or cyclohexanone, an amine such as triethylamine, aniline or phenethylamine, an amide such as formamide, N,N-dimethylformamide, or N,N-dimethylacetamide, a nitrile such as acetonitrile, malononitrile, or benzonitrile, a sulfoxide such as dimethyl sulfoxide, and water, of which an aromatic hydrocarbon such as toluene, xylene, or mesitylene and a halogenated aromatic hydrocarbon such as chlorobenzene or o-dichlorobenzene are preferable and an aromatic hydrocarbon such as toluene, xylene, or mesitylene is more preferable. Each of the solvents may be used alone, or two or more of these bases may be used in combination, as appropriate.

The amount of the solvent used is not particularly limited, and is selected, as appropriate, from the range of generally 0.5 to 100 volumes, preferably 1 to 50 volumes, and more preferably 2 to 40 volumes to 1 volume of the compound having the formula (4).

This reaction is preferably carried out in an inert gas atmosphere. Specific examples of the inert gas include argon gas and nitrogen gas.

The reaction temperature is selected, as appropriate, from the range of generally 0 to 250° C., preferably 10 to 200° C., and more preferably 20 to 180° C.

The reaction time naturally varies depending on the amines, the solvent, the reaction temperature, and other conditions, and is selected, as appropriate, from the range of generally 1 minute to 48 hours, preferably 5 minutes to 24 hours, and more preferably 10 minutes to 15 hours.

If necessary, the thus obtained ruthenium complex having the formula (5) may be subjected to post treatments, isolation, and purification. Examples of methods for the post treatments include concentration, solvent exchange, washing, extraction, back-extraction, filtration, and crystallization by adding a poor solvent. These methods can be performed alone or in combination.

EXAMPLES

The present invention is described in more detail by the following examples. However, the present invention is not limited by the following examples.

1) Proton nuclear magnetic resonance spectroscopy ($^1$H NMR): Varian Mercury plus Model 300 spectrometer (resonance frequency: 300 MHz, manufactured by Varian, Inc.) or Model 400MR DD2 spectrometer (resonance frequency: 400 MHz, manufactured by Agilent Technologies, Inc.)

Internal standard: tetramethylsilane (0 ppm (singlet peak)) or residual non-deuterated solvent (dichloromethane: 5.32 ppm (triplet peak), or chloroform: 7.26 ppm (singlet peak))

2) Carbon 13 nuclear magnetic resonance spectroscopy ($^{13}$C NMR): Varian Mercury plus Model 300 spectrometer (resonance frequency: 75 MHz, manufactured by Varian, Inc.) or Model 400MR DD2 spectrometer (resonance frequency: 100 MHz, manufactured by Agilent Technologies, Inc.)

Internal standard: chloroform (77 ppm (triplet peak))

3) Phosphorus 31 nuclear magnetic resonance spectroscopy ($^{31}$P NMR): Varian Mercury plus Model 300 spectrometer (resonance frequency: 121 MHz, manufactured by Varian, Inc.) or Model 400MR DD2 spectrometer (resonance frequency: 161 MHz, manufactured by Agilent Technologies, Inc.)

External standard: phosphoric acid (0 ppm (singlet peak)) solution in $D_2O$ Example 1

Synthesis of N,N-bis[2-(dicyclohexylphosphino)ethyl]amine-bisborane Complex

[Chemical Formula 12]

Process 1: Synthesis of 3-(2-chloroethyl)-2-oxazolidinone

[Chemical Formula 13]

(Setup and Reaction) A magnetic stirrer bar, a thermometer, and a three-way cock were attached to a 500 mL four-necked round-bottom flask, and the flask was purged with nitrogen. Then, N,N-bis(chloroethyl)amine hydrochloride (40.0 g, 224 mmol, 1.0 equivalent), methanol (MeOH) (120 mL), and triethylamine ($Et_3N$) (47.6 g, 471 mmol, 2.1 equivalents) were introduced sequentially. Carbon dioxide ($CO_2$) gas was passed through the obtained solution at 20 to 30° C. for 30 minutes.

(Post Treatment, Isolation, and Purification) The reaction mixture was concentrated in vacuo, and then toluene (120 mL) was added, and the mixture was then concentrated in vacuo. Toluene (120 mL) was further added, and the mixture was concentrated in vacuo. After methanol was sufficiently removed, toluene (120 mL) was added again. The obtained white suspension was filtered by suction, and the residue was washed with toluene. The filtrate was concentrated in vacuo, and the residue was purified by distillation (boiling point: 145° C. (5 mmHg)), thus obtaining 30.7 g of the title compound as a pale yellow liquid. The isolated yield was 91.6%.

$^1$H NMR (300 MHz, deuterated chloroform ($CDCl_3$)): δ=4.38 (ddd, J=0.9, 6.3, 7.8 Hz, 2H), 3.79-3.67 (m, 4H), 3.66-3.59 (m, 2H).

$^{13}$C NMR (75 MHz, $CDCl_3$): δ=158.38, 62.01, 46.19, 45.70, 42.03.

Process 2: Synthesis of dicyclohexylphosphine-borane Complex

[Chemical Formula 14]

(Setup and Reaction) A magnetic stirrer bar, a thermometer, and a three-way cock were attached to a 1 L four-necked round-bottom flask, and the flask was purged with nitrogen. Then, a borane-tetrahydrofuran solution ($BH_3$-THF solution, concentration: 0.9 mol/L, 212 mL, 191 mmol, 1.05 equivalents) was introduced, and cooled to 5° C. in an ice-water bath. Subsequently, dicyclohexylphosphine (36.0 g, 182 mmol, 1.0 equivalent) was added dropwise via a syringe over 30 minutes so that the internal temperature was maintained at not more than 10° C.

(Post Treatment, Isolation, and Purification) The reaction mixture was added with water (0.7 mL, 0.2 equivalents) to quench the reaction, and the mixture was concentrated in vacuo. Subsequently, toluene (288 mL) and water (216 mL) were added. After stirring, the mixture was allowed to stand, and the aqueous layer was separated. After concentrating the organic layer in vacuo, dehydrated tetrahydrofuran (144 mL) was added to obtain a tetrahydrofuran solution of the title compound.

$^{31}$P NMR (161 MHz, tetrahydrofuran): δ=18.6-17.8 (m)

Process 3: Synthesis of N,N-bis[2-(dicyclohexylphosphino)ethyl]amine-bisborane Complex

[Chemical Formula 15]

(Setup and Reaction) A magnetic stirrer bar, a thermometer, a dropping funnel, and a three-way cock were attached to a 1 L four-necked round-bottom flask, and the flask was purged with nitrogen. Then, a tetrahydrofuran solution (182 mmol, 1.0 equivalent) of a dicyclohexylphosphine-borane complex was introduced, and cooled to 5° C. in an ice-water bath. Subsequently, an n-hexane solution of n-butyllithium (n-BuLi) (concentration: 1.60 mol/L, 108 mL, 173 mmol, 0.95 equivalents) was placed in a dropping funnel, and added dropwise to the solution at such a rate that the internal temperature was maintained at not more than 10° C. over 30 minutes. The ice-water bath was removed, and the temperature was returned to 20° C. Then, 3-(2-chloroethyl)-2-oxazolidinone (12.2 g, 81.7 mmol, 0.45 equivalents) and dehydrated tetrahydrofuran (36.0 mL) were placed in a dropping funnel, and added dropwise at such a rate that the internal temperature was maintained at not more than 25° C. over 30 minutes, followed by stirring at room temperature for 2 hours.

(Post Treatment, Isolation, and Purification) The reaction mixture was concentrated in vacuo, and then toluene (288 mL) and water (360 mL) were added. After stirring, the mixture was allowed to stand, and the aqueous layer was separated. The organic layer was again washed with water (108 mL) and concentrated in vacuo. Analysis of the obtained crude product by NMR showed that the crude product was a 85/15 mixture of a complex with two $BH_3$ molecules (a bisborane complex) and a complex with three $BH_3$ molecules (a trisborane complex). The obtained crude product was recrystallized from toluene to obtain 14.1 g of the title compound as a white powder. Isolated yield: 69.8%.

$^1$H NMR (400 MHz, deuterated chloroform ($CDCl_3$)): δ=2.87-2.81 (m, 4H), 1.90-1.68 (m, 28H), 1.38-1.21 (m, 20H).

$^{31}$P NMR (161 MHz, deuterated chloroform ($CDCl_3$)): δ=22.5 (d, J=64.2 Hz, 2P)

Reference Example 1

Synthesis of N,N-bis[2-(dicyclohexylphosphino)ethyl]amine-trisborane Complex

[Chemical Formula 16]

(Setup and Reaction) A magnetic stirrer bar, a thermometer, and a three-way cock were attached to a 100 mL four-necked round-bottom flask, and the flask was purged with nitrogen. Then, an N,N-bis[2-(dicyclohexylphosphino)ethyl]amine-bisborane complex (10.0 g, 20.3 mmol, 1.0 equivalent) and tetrahydrofuran (20 mL) were introduced, and cooled to 5° C. in an ice-water bath. Subsequently, a borane-tetrahydrofuran solution ($BH_3$-THF solution, concentration: 0.9 mol/L, 24.8 mL, 22.3 mmol, 1.1 equivalents) was added dropwise via a syringe over 30 minutes so that the internal temperature was maintained at not more than 10° C.

(Post Treatment, Isolation, and Purification) The reaction mixture was concentrated in vacuo, and then toluene (50 mL) and water (25 mL) were added. After stirring, the mixture was allowed to stand, and the aqueous layer was separated. The organic layer was again washed with water (20 mL) and concentrated in vacuo. The obtained residue was recrystallized from toluene to obtain 6.1 g of the title compound as a white powder. Isolated yield: 58.8%

$^1$H NMR (400 MHz, deuterated chloroform ($CDCl_3$)): δ=4.49 (br s, 1H), 2.99-2.90 (m, 4H), 2.36-2.04 (m, 4H), 1.86-1.70 (m, 24H), 1.43-1.24 (m, 20H).

$^{31}$P NMR (161 MHz, deuterated chloroform ($CDCl_3$)): δ=22.8 (d, J=49.6 Hz, 2P)

Example 2

Synthesis of Carbonyl chlorohydride{bis[2-(dicyclohexylphosphino)ethyl]amine}ruthenium(II)

[Chemical Formula 17]

(Setup and Reaction) A magnetic stirrer bar, a thermometer, a condenser, and a three-way cock were attached to a 50 mL four-necked round-bottom flask, and the flask was purged with nitrogen. Then, carbonylchlorohydrido tris(triphenylphosphine)ruthenium(II) (RuHCl(CO)(PPh$_3$)$_3$) (2.00 g, 2.10 mmol, 1.0 equivalent), N,N-bis[2-(dicyclohexylphosphino)ethyl]amine-bisborane complex (1.14 g, 2.31 mmol, 1.1 equivalents), 1,4-diazabicyclo[2.2.2]octane (DABCO) (705 mg, 6.29 mmol, 3.0 equivalents), and toluene (20 mL) were introduced sequentially, and the mixture was stirred under reflux for 1 hour.

(Post Treatment, Isolation, and Purification) The suspension obtained after the reaction was filtered by suction, and then the crystals obtained by filtration were washed with toluene (20 mL), and dried by heating under reduced pressure, thus obtaining 1.40 g of the title compound as a pale yellow powder. Isolated yield: 100%.

Figure 1:
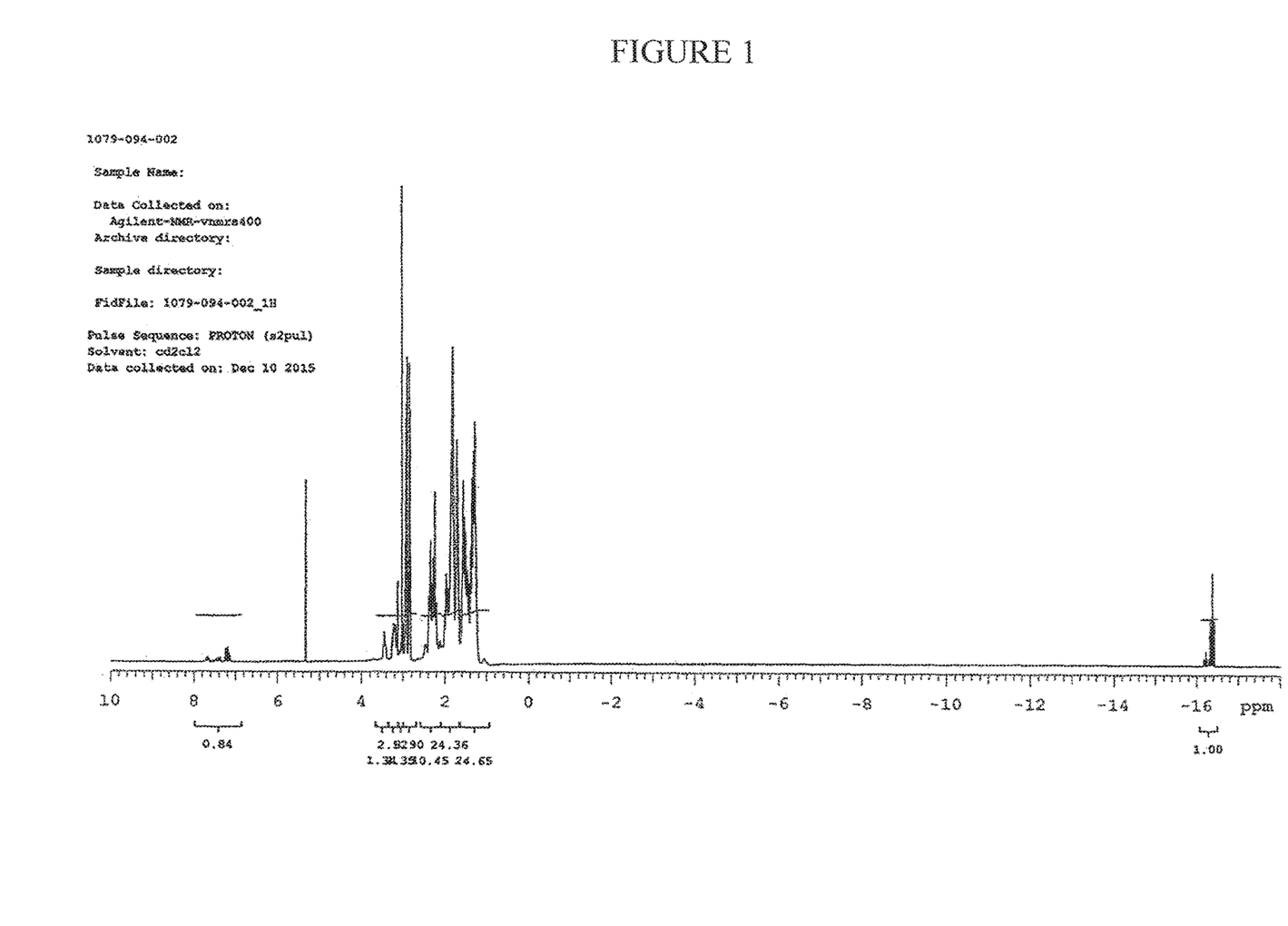
FIG. 1 shows a $^1H$ NMR chart of carbonyl chlorohydride{bis[2-(dicyclohexylphosphino)ethyl]amine}ruthenium(II) (Example 2).

$^1$H NMR (400 MHz, deuterated methylene chloride ($CD_2Cl_2$)): see FIG. 1

$^{31}$P NMR (161 MHz, deuterated methylene chloride (CD$_2$Cl$_2$)): δ=65.5-65.0 (m, 2P)

(Example 3) Synthesis of Carbonyl chlorohydride{bis[2-(dicyclohexylphosphino)ethyl]amine}ruthenium(II)

[Chemical Formula 18]

As in Example 2 described above, 1.40 g of the title compound was obtained as a pale yellow powder from carbonylchlorohydrido tris(triphenylphosphine)ruthenium (II) (RuHCl(CO)(PPh$_3$)$_3$) (2.00 g, 2.10 mmol, 1.0 equivalent), a mixture of an N,N-bis[2-(dicyclohexylphosphino)ethyl]amine-bisborane complex (0.85 g, 1.72 mmol, 0.82 equivalents) and an N,N-bis[2-(dicyclohexylphosphino)ethyl]amine-trisborane complex (0.29 g, 0.57 mmol, 0.27 equivalents), and 1,4-diazabicyclo[2.2.2]octane (DABCO) (705 mg, 6.29 mmol, 3.0 equivalents). Isolated yield: 100%

Example 4

Synthesis of N,N-bis[2-(bis tert-butylphosphino)ethyl]amine-diborane Complex

[Chemical Formula 19]

Process 4-1: Synthesis of Bis tert-butylphosphine-borane Complex

[Chemical Formula 20]

(Setup and Reaction) A magnetic stirrer bar, a thermometer, and a three-way cock were attached to a 100 L four-necked round-bottom flask, and the flask was purged with nitrogen. Then, a borane-tetrahydrofuran solution (BH$_3$-THF solution, concentration: 0.9 mol/L, 21.2 mL, 19.1 mmol, 1.05 equivalents) was introduced, and cooled to 5° C. in an ice-water bath. Subsequently, bis(tert-butyl)phosphine (2.66 g, 18.2 mmol, 1.0 equivalent) was added dropwise via a syringe over 30 minutes so that the internal temperature was maintained at not more than 10° C.

(Post Treatment, Isolation, and Purification) Water (0.2 mL) was added to the reaction mixture to quench the reaction, and the reaction mixture was concentrated in vacuo. Then, ethyl acetate (30 mL) and water (10 mL) were added. After stirring, the mixture was allowed to stand, and the aqueous layer was separated. The aqueous layer was extracted again with ethyl acetate (10 mL×twice), and the combined organic phases were dried with MgSO$_4$ and then filtered, followed by concentrating the filtrate in vacuo. The obtained crude product was purified by a silica gel column to obtain 2.62 g of the title compound as a white powder. Isolated yield: 90.0%.

Process 4-2, 3: Synthesis of N,N-bis[2-(bis tert-butylphosphino)ethyl]amine-diborane Complex

[Chemical Formula 21]

(Setup and Reaction) A magnetic stirrer bar, a thermometer, a dropping funnel, and a three-way cock were attached to a 100 mL four-necked round-bottom flask, and the flask was purged with nitrogen. Then, 1.95 g of bis tert-butylphosphine-borane complex (12.18 mmol, 1.0 equivalent) and dehydrated tetrahydrofuran (10.0 mL) were introduced, and cooled to 5° C. in an ice-water bath. Subsequently, an n-hexane solution of n-butyllithium (n-BuLi) (concentration: 1.64 mol/L, 7.06 mL, 11.57 mmol, 0.95 equivalents) was placed in a dropping funnel, and added dropwise to the solution at such a rate that the internal temperature was maintained at not more than 10° C. over 30 minutes. The ice-water bath was removed, and the temperature was returned to 20° C. Then, 3-(2-chloroethyl)-2-oxazolidinone (0.82 g, 5.48 mmol, 0.45 equivalents) and dehydrated tetrahydrofuran (2.5 mL) were placed in a dropping funnel, and added dropwise at such a rate that the internal temperature was maintained at not more than 25° C. over 30 minutes, followed by stirring at room temperature for 2 hours.

(Post Treatment, Isolation, and Purification) The reaction mixture was concentrated in vacuo, and then ethyl acetate (50 mL) and water (30 mL) were added. After stirring, the mixture was allowed to stand, and the aqueous layer was separated. The aqueous layer was extracted again with ethyl acetate (10 mL×twice), and the combined organic phases were dried with MgSO$_4$ and then filtered, followed by concentrating the filtrate in vacuo. The obtained crude product was purified by a silica gel column to obtain 1.64 g of the title compound as a white powder. Isolated yield: 77.0%.

$^1$H NMR (400 MHz, deuterated chloroform (CDCl$_3$)): δ=2.98-2.92 (m, 4H), 1.86-1.79 (m, 4H), 1.26 (d, 36H).

$^{31}$P NMR (161 MHz, deuterated chloroform (CDCl$_3$)): δ=40.7 (d, J=67.1 Hz, 2P)

Process 4-4: Synthesis of Carbonyl chlorohydride{bis[2-(bis tert-butylphosphino)ethyl]amine}ruthenium(II)

[Chemical Formula 22]

tert-Bu-Ru-MACHO (Setup and Reaction) A magnetic stirrer bar and a condenser were attached to a 50 mL Schlenk tube, and the Schlenk tube was purged with nitrogen. Then, carbonylchlorohydrido tris(triphenylphosphine)ruthenium(II) (RuHCl(CO)(PPh$_3$)$_3$) (1.67 g, 1.75 mmol, 1.0 equivalent), N,N-bis[2-(bis tert-butylphosphino)ethyl]amine-diborane complex (0.75 g, 1.93 mmol, 1.1 equivalents), 1,4-diazabicyclo[2.2.2]octane (DABCO) (590 mg, 5.25 mmol, 3.0 equivalents), and toluene (15 mL) were introduced sequentially, and the mixture was stirred under reflux for 1 hour.

(Post Treatment, Isolation, and Purification) The suspension obtained after the reaction was filtered by suction, and then the crystals obtained by filtration were washed with toluene (15 mL), and dried by heating under reduced pressure, thus obtaining 0.74 g of the title compound as a gray powder. Isolated yield: 80.4%.

Figure 2:
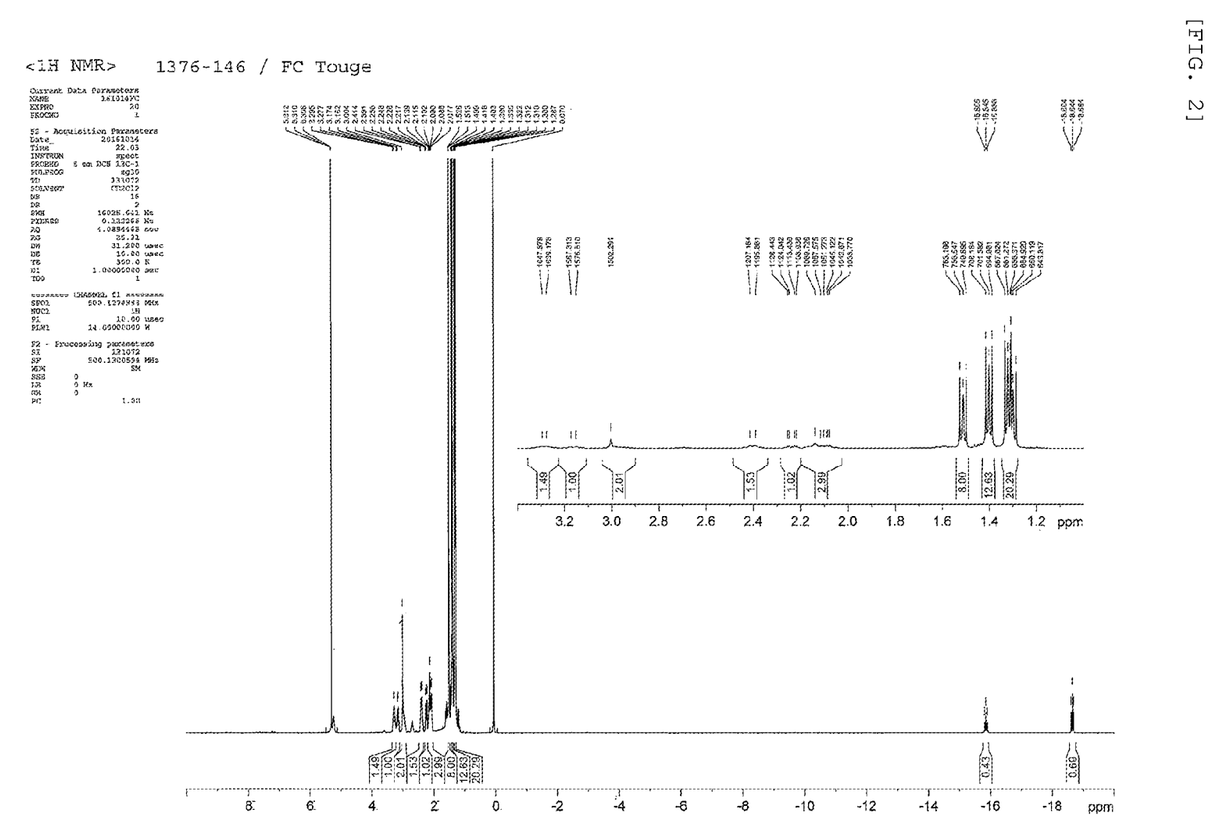
FIG. 2 shows a $^1H$ NMR chart of carbonyl chlorohydride{bis[2-(bis tert-butylphosphino)ethyl]amine}ruthenium(II) (Example 4).

$^1$H NMR (400 MHz, deuterated methylene chloride (CD$_2$Cl$_2$)): see FIG. 2

$^{31}$P NMR (161 MHz, deuterated methylene chloride (CD$_2$Cl$_2$)): δ=86.6-86.2 (m, 2P)

Example 5

Synthesis of N,N-bis[2-(bisisopropylphosphino)ethyl]amine-diborane Complex

[Chemical Formula 23]

iso-Pr-Ru-MACHO

Process 5-1: Synthesis of Bisisopropylphosphine

[Chemical Formula 24]

(Setup and Reaction)

A magnetic stirrer bar, a thermometer, and a three-way cock were attached to a 300 mL four-necked round-bottom flask, and the flask was purged with nitrogen. Then, bisisopropylphosphine chloride (5.0 g, 32.8 mmol, 1.0 equivalent) and diethyl ether (25 mL) were introduced, and cooled to 5° C. in an ice-water bath. Subsequently, an ether solution of LiAlH$_4$ (concentration: 1.0 mol/L, 32.8 mL, 32.8 mmol, 1.0 equivalent) was added dropwise over 30 minutes so that the internal temperature was maintained at not more than 10° C.

(Post Treatment, Isolation, and Purification) Water (6.0 mL) was added to the reaction mixture to quench the reaction, and the reaction mixture was dried with MgSO$_4$ and then filtered. The filtrate was concentrated in vacuo to obtain 3.0 g of bisisopropylphosphine. (Yield 77.5%)

Process 5-2: Synthesis of bisisopropylphosphine-borane Complex

[Chemical Formula 25]

(Setup and Reaction)

A magnetic stirrer bar, a thermometer, and a three-way cock were attached to a 300 mL four-necked round-bottom flask, and the flask was purged with nitrogen. Then, a borane-tetrahydrofuran solution (BH$_3$-THF solution, concentration: 0.9 mol/L, 100 mL, 90 mmol, 3.5 equivalents) was introduced, and cooled to 5° C. in an ice-water bath. Subsequently, bisisopropylphosphine (3.0 g, 25.4 mmol, 1.0 equivalent) was added dropwise via a syringe over 30 minutes so that the internal temperature was maintained at not more than 10° C.

(Post Treatment, Isolation, and Purification) Water (0.2 mL) was added to the reaction mixture to quench the reaction, and the reaction mixture was concentrated in vacuo. Then, ethyl acetate (50 mL) and water (10 mL) were added. After stirring, the mixture was allowed to stand, and the aqueous layer was separated. The aqueous layer was extracted again with ethyl acetate (20 mL×twice), and the combined organic phases were dried with MgSO$_4$ and then filtered, followed by concentrating the filtrate in vacuo. The obtained crude product was purified by a silica gel column to obtain 1.0 g of the title compound as a colorless liquid. Isolated yield: 24.6%.

$^{31}$P NMR (161 MHz, deuterated chloroform): δ=27.4-26.5 (m)

Process 5-3, 4: Synthesis of N,N-bis[2-(bisisopropylphosphino)ethyl]amine-diborane Complex

[Chemical Formula 26]

(Setup and Reaction) A magnetic stirrer bar, a thermometer, a dropping funnel, and a three-way cock were attached to a 100 mL four-necked round-bottom flask, and the flask was purged with nitrogen. Then, a bisisopropylphosphine-borane complex (1.2 g, 9.1 mmol, 1.0 equivalent) and dehydrated tetrahydrofuran (10 mL) were introduced, and cooled to 5° C. in an ice-water bath. Subsequently, an n-hexane solution of n-butyllithium (n-BuLi) (concentration: 1.64 mol/L, 5.27 mL, 8.64 mmol, 0.95 equivalents) was placed in a dropping funnel, and added dropwise to the solution at such a rate that the internal temperature was maintained at not more than 10° C. over 30 minutes. The ice-water bath was removed, and the temperature was returned to 20° C. Then, 3-(2-chloroethyl)-2-oxazolidinone (0.61 g, 4.09 mmol, 0.45 equivalents) and dehydrated tetrahydrofuran (2.5 mL) were placed in a dropping funnel, and added dropwise at such a rate that the internal temperature was maintained at not more than 25° C. over 30 minutes, followed by stirring at room temperature for 2 hours.

(Post Treatment, Isolation, and Purification) The reaction mixture was concentrated in vacuo, and then ethyl acetate (50 mL) and water (30 mL) were added. After stirring, the mixture was allowed to stand, and the aqueous layer was separated. The aqueous layer was extracted again with ethyl acetate (10 mL×twice), and the combined organic phases were dried with MgSO$_4$ and then filtered, followed by concentrating the filtrate in vacuo. The obtained crude product was purified by a silica gel column to obtain 0.1 g of the title compound as a white powder. Isolated yield: 8.0%.

$^1$H NMR (400 MHz, deuterated chloroform (CDCl$_3$)): δ=3.50-3.40 (m, 4H), 2.10-2.00 (m, 4H), 1.90-1.92 (m, 4H), 1.28-1.18 (m, 24H).

$^{31}$P NMR (161 MHz, deuterated chloroform (CDCl$_3$)): δ=30.2 (d, J=68.6 Hz, 2P)

Process 5-5: Synthesis of Carbonyl chlorohydride{bis[2-(bisisopropylphosphino)ethyl]amine}ruthenium(II)

[Chemical Formula 27]

-continued iso-Pr-Ru-MACHO (Setup and Reaction) A magnetic stirrer bar and a condenser were attached to a 50 mL Schlenk tube, and the Schlenk tube was purged with nitrogen. Then, carbonylchlorohydrido tris(triphenylphosphine)ruthenium(II) (RuHCl(CO)(PPh$_3$)$_3$) (0.285 g, 0.30 mmol, 1.0 equivalent), N,N-bis[2-(dicyclohexylphosphino)ethyl]amine-diborane complex (0.1 g, 0.30 mmol, 1.0 equivalent), 1,4-diazabicyclo[2.2.2]octane (DABCO) (168 mg, 1.50 mmol, 5.0 equivalents), and toluene (3 mL) were introduced sequentially, and the mixture was stirred under reflux for 1 hour.

(Post Treatment, Isolation, and Purification) The suspension obtained after the reaction was filtered by suction, and then the crystals obtained by filtration were washed with toluene (20 mL), and dried by heating under reduced pressure, thus obtaining 21 mg of the title compound as a pale yellow powder. Isolated yield: 15%.

$^1$H NMR (400 MHz, deuterated methylene chloride (CD$_2$Cl$_2$)): δ=3.42 (br, 1H), 3.33-3.15 (m, 2H), 2.70-2.62 (m, 2H), 2.36-2.20 (m, 4H), 1.84-1.72 (m, 4H), 1.49-1.01 (m, 24H), -16.30 (t, J=18.0 Hz, 1H)

$^{31}$P NMR (161 MHz, deuterated methylene chloride (CD$_2$Cl$_2$)): 75.1 (s, 2P)

INDUSTRIAL APPLICABILITY

The present invention provides a production method in which a ruthenium metal complex containing, as a ligand, N,N-bis(2-dialkylphosphinoethyl)amines having excellent performance such as catalytic activity in a hydrogenation reaction of a carbonyl compound, a dehydrogenation reaction of alcohols, etc. can be produced in a simple manner and high yield. The present invention further provides an N,N-bis(2-dialkylphosphinoethyl)amine-borane complex which is useful as a ligand raw material and a novel method for safely and practically producing the same. The N,N-bis(2-dialkylphosphinoethyl)amine-borane complex is stable to air and can be easily purified by, for example, column chromatography or recrystallization, and by reacting this complex with a ruthenium precursor in the presence of amines, a ruthenium metal complex can be easily and safely produced in high yield by a short process; therefore, it is suitable for industrial application.

Accordingly, the N,N-bis(2-dialkylphosphinoethyl) amine-borane complex of the present invention, the production method therefor, and a method for producing a ruthenium complex using an N,N-bis(2-dialkylphosphinoethyl) amine-borane complex is useful in the field of organic industrial chemistry.

The invention claimed is:

1. A method for producing a compound having the following formula (3):

wherein the solid line represents a single bond; B represents a boron atom, C represents a carbon atom, H represents a hydrogen atom, N represents a nitrogen atom, and P represents a phosphorus atom; $R^1$ and $R^2$ each independently represent an optionally substituted alkyl group or an optionally substituted cycloalkyl group, wherein $R^1$ and $R^2$, which are adjacent to each other, may bind together to form an optionally substituted ring; $R^3$, $R^4$, $R^5$, $R^6$, $R^7$, $R^8$, $R^9$ and $R^{10}$ each independently represent a hydrogen atom or a group selected from the group consisting of an optionally substituted alkyl group, an optionally substituted cycloalkyl group, an optionally substituted alkenyl group, an optionally substituted aryl group, and an optionally substituted aralkyl group, wherein any two of $R^3$ to $R^{10}$ may bind together to form an optionally substituted ring; n=2 to 3, and BH$_3$ is coordinated to a nitrogen atom or phosphorus atom, the method comprising: reacting a compound having the following formula (1):

wherein the solid line represents a single bond, and the double line represents a double bond; C represents a carbon atom, N represents a nitrogen atom, and O represents an oxygen atom; LG represents a leaving group; $R^3$, $R^4$, $R^5$, $R^6$, $R^7$, $R^8$, $R^9$ and $R^{10}$ each independently represent a hydrogen atom or a group selected from the group consisting of an optionally substituted alkyl group, an optionally substituted cycloalkyl group, an optionally substituted alkenyl group, an optionally substituted aryl group, and an optionally substituted aralkyl group, wherein any two of $R^3$ to $R^{10}$ may bind together to form an optionally substituted ring, with a phosphorus compound having the following formula (2):

wherein the solid line represents a single bond, and the dashed line represents a coordination bond; B represents a boron atom, H represents a hydrogen atom, and P represents a phosphorus atom; $R^1$ and $R^2$ each independently represent an optionally substituted alkyl group or an optionally substituted cycloalkyl group, wherein R¹ and R² may bind together to form an optionally substituted ring, in the presence of bases.

2. The method according to claim 1, wherein R³, R⁴, R⁵, R⁶, R⁷, R⁸, R⁹ and R¹⁰ are hydrogen atoms.

3. The method according to claim 1 or 2, wherein R¹ and R² are groups each independently selected from the group consisting of an isopropyl group, a cyclohexyl group, and a tert-butyl group.

4. The method according to claim 1, wherein LG is a halogen atom or a group selected from the group consisting of a methanesulfonyloxy group (OMs), a p-toluenesulfonyloxy group (OTs), a benzenesulfonyloxy group (OSO₂C₆H₅), and a trifluoromethanesulfonyloxy group (OTf).

5. The method according to claim 1, wherein one of the bases is an alkyllithium.

6. A method for producing a ruthenium complex having the following formula (5):

[Chemical Formula 6]

(5)

wherein the solid line represents a single bond, the triple line represents a triple bond, and the dashed line represents a coordination bond; C represents a carbon atom, H represents a hydrogen atom, N represents a nitrogen atom, O represents an oxygen atom, P represents a phosphorus atom, and Ru represents a ruthenium atom; X represents an anionic group; R¹ and R² each independently represent an optionally substituted alkyl group or an optionally substituted cycloalkyl group, wherein R¹ and R², which are adjacent to each other, may bind together to form an optionally substituted ring; R³, R⁴, R⁵, R⁶, R⁷, R⁸, R⁹ and R¹⁰ each independently represent a hydrogen atom or a group selected from the group consisting of an optionally substituted alkyl group, an optionally substituted cycloalkyl group, an optionally substituted alkenyl group, an optionally substituted aryl group, and an optionally substituted aralkyl group, wherein any two of R³ to R¹⁰ may bind together to form an optionally substituted ring, the method comprising: reacting a compound having the following formula (3):

(3)

wherein the solid line represents a single bond; B represents a boron atom, C represents a carbon atom, H represents a hydrogen atom, N represents a nitrogen atom, and P represents a phosphorus atom; R¹ and R² each independently represent an optionally substituted alkyl group or an optionally substituted cycloalkyl group, wherein R¹ and R², which are adjacent to each other, may bind together to form an optionally substituted ring; R³, R⁴, R⁵, R⁶, R⁷, R⁸, R⁹ and R¹⁰ each independently represent a hydrogen atom or a group selected from the group consisting of an optionally substituted alkyl group, an optionally substituted cycloalkyl group, an optionally substituted alkenyl group, an optionally substituted aryl group, and an optionally substituted aralkyl group, wherein any two of R³ to R¹⁰ may bind together to form an optionally substituted ring; n=2 to 3, and BH₃ is coordinated to a nitrogen atom or phosphorus atom, with a ruthenium compound having the following formula (4):

(4)

wherein the solid line represents a single bond, the triple line represents a triple bond, and the dashed line represents a coordination bond; C represents a carbon atom, H represents a hydrogen atom, O represents an oxygen atom, and Ru represents a ruthenium atom; X represents an anionic group; and L¹, L², and L³ each independently represent a monodentate ligand, in the presence of amines.

7. The method according to claim 6, wherein R³, R⁴, R⁵, R⁶, R⁷, R⁸, R⁹ and R¹⁰ are hydrogen atoms.

8. The method according to claim 6 or 7, wherein R¹ and R² are groups each independently selected from the group consisting of an isopropyl group, a cyclohexyl group, and a tert-butyl group.

9. The method according to claim 6, wherein L¹, L², and L³ are tertiary phosphines.

10. The method according to claim 6, wherein X is a halogen atom.

11. A compound having the following formula (3):

(3)

wherein the solid line represents a single bond; B represents a boron atom, C represents a carbon atom, H represents a hydrogen atom, N represents a nitrogen atom, and P represents a phosphorus atom; R¹ and R² each independently represent an optionally substituted alkyl group or an optionally substituted cycloalkyl group, wherein R¹ and R², which are adjacent to each other, may bind together to form an optionally substituted ring; R³, R⁴, R⁵, R⁶, R⁷, R⁸, R⁹ and R¹⁰ each independently represent a hydrogen atom or a group selected from the group consisting of an optionally substituted alkyl group, an optionally substituted cycloalkyl group, an optionally substituted alkenyl group, an optionally substituted aryl group, and an optionally substituted aralkyl group, wherein any two of $R^3$ to $R^{10}$ may bind together to form an optionally substituted ring; n=2 to 3, and $BH_3$ is coordinated to a nitrogen atom or phosphorus atom.

* * * * *